(12) United States Patent
Querio

(10) Patent No.: US 8,393,595 B2
(45) Date of Patent: Mar. 12, 2013

(54) ELECTROMECHANICAL ACTUATOR DEVICE, IN PARTICULAR FOR THE ACTUATION OF FLUID VALVES

(75) Inventor: Leo Querio, Turin (IT)

(73) Assignee: Elbi International S.p.A., Turin (IT)

( * ) Notice: Subject to any disclaimer, the term of this patent is extended or adjusted under 35 U.S.C. 154(b) by 769 days.

(21) Appl. No.: 12/593,229

(22) PCT Filed: Mar. 26, 2008

(86) PCT No.: PCT/IB2008/051128
§ 371 (c)(1),
(2), (4) Date: Sep. 25, 2009

(87) PCT Pub. No.: WO2008/117251
PCT Pub. Date: Oct. 2, 2008

(65) Prior Publication Data
US 2010/0102260 A1  Apr. 29, 2010

(30) Foreign Application Priority Data

Mar. 27, 2007 (IT) .............................. TO20070044 U

(51) Int. Cl.
*F16K 31/02* (2006.01)
(52) U.S. Cl. ............. 251/129.12; 251/129.07; 310/68 R
(58) Field of Classification Search ............. 251/129.01, 251/129.07, 129.11, 129.12; 310/68 R, 71, 310/68 E, 75 R, 11, 26–28, 31, 32
See application file for complete search history.

(56) References Cited

U.S. PATENT DOCUMENTS
5,568,911 A * 10/1996 Kim .................... 251/129.12

FOREIGN PATENT DOCUMENTS
GB       2316152 A       2/1998

* cited by examiner

*Primary Examiner* — John K Fristoe, Jr.
*Assistant Examiner* — Marina Tietjen
(74) *Attorney, Agent, or Firm* — Sughrue Mion, PLLC

(57) ABSTRACT

The device (1) includes a housing (2) in which an electric motor (5) is secured, the shaft (6) of this motor being coupled to a rotary control member (11) having on one surface a cam profile (11c) cooperating with a coordinated profile (20d) of a controlled member (20) which may move in translation in the housing (2) such that when the motor (5) is actuated, the rotation of the rotary control member (11) is adapted to cause the controlled member (20) to move in translation into a first position remote from the control member (11) or to enable this controlled member (20) to move in translation into a second position close to the control member (11). The housing (2) further bears a first and a second electrical switch (31, 32) connected to the motor (5) and comprising respective fixed contacts (31b, 32b) and a single common moving contact member (33), made from an electrically conducting material, with which two integral feeler members (33a, 33b; 50, 51) are associated and cooperate directly with associated cam profiles of the rotary control member (11).

5 Claims, 8 Drawing Sheets

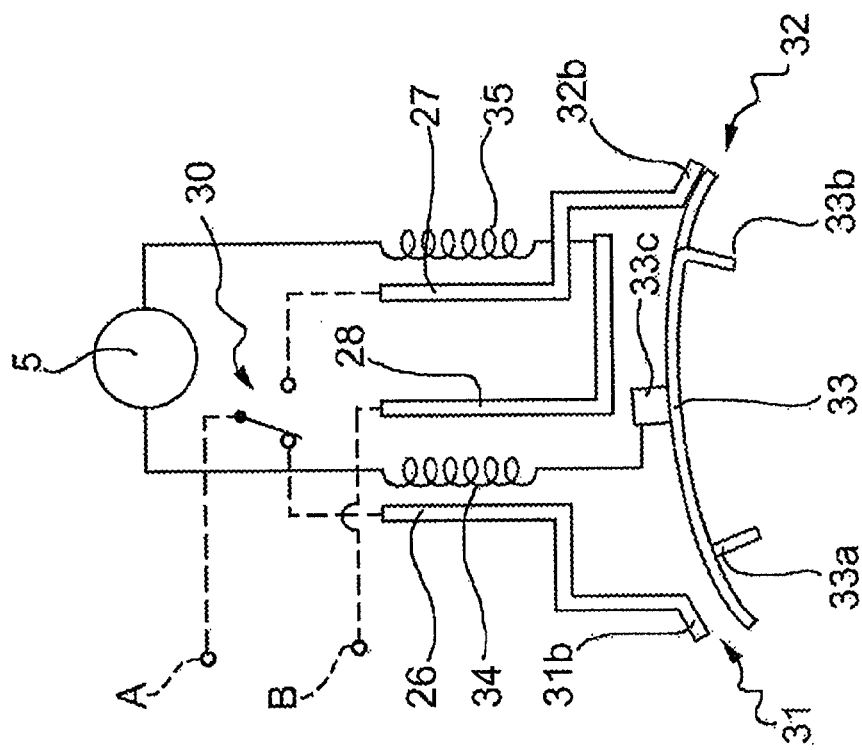
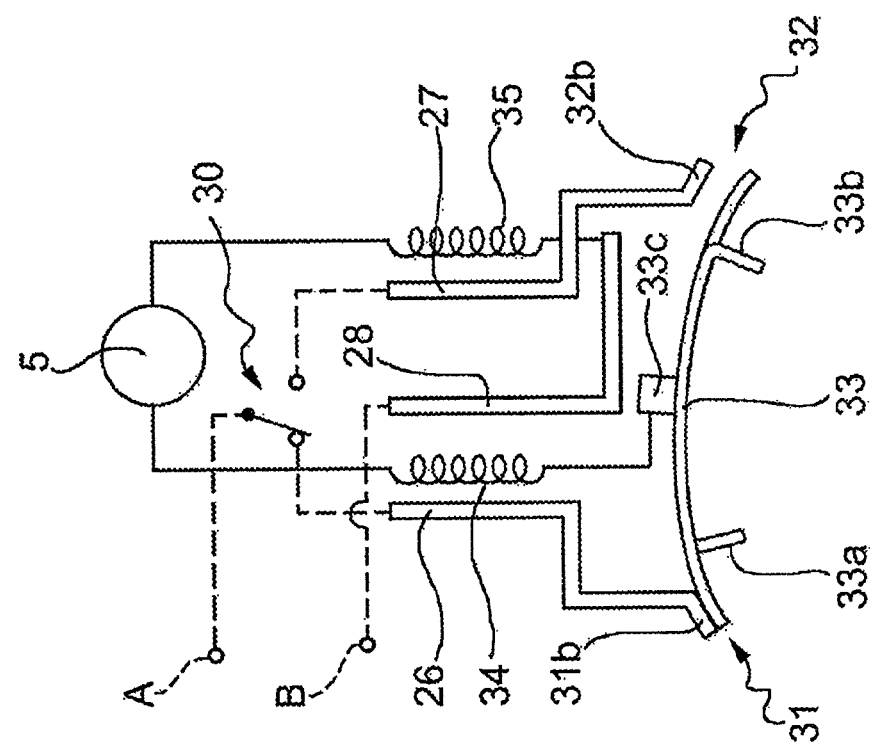

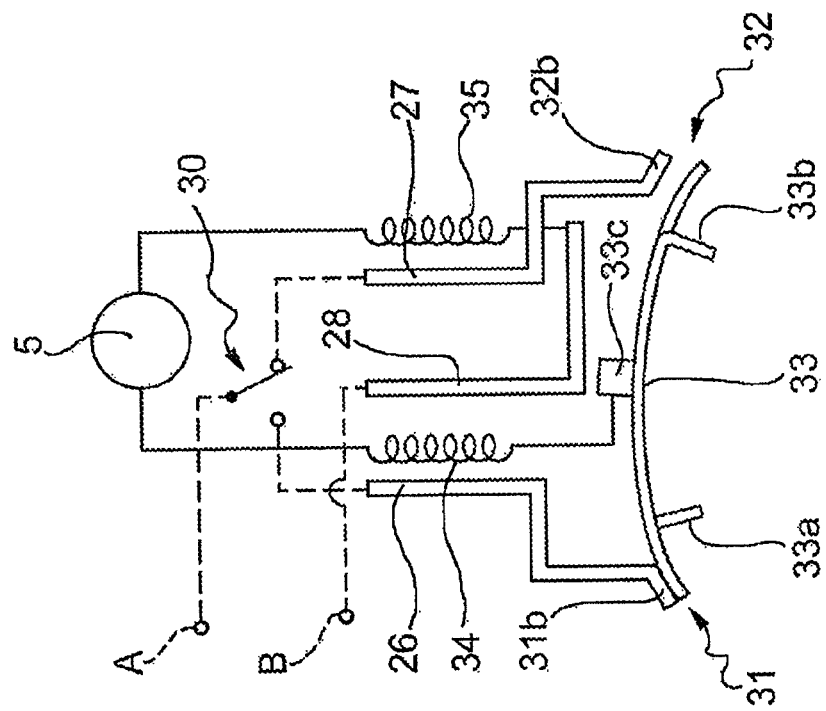
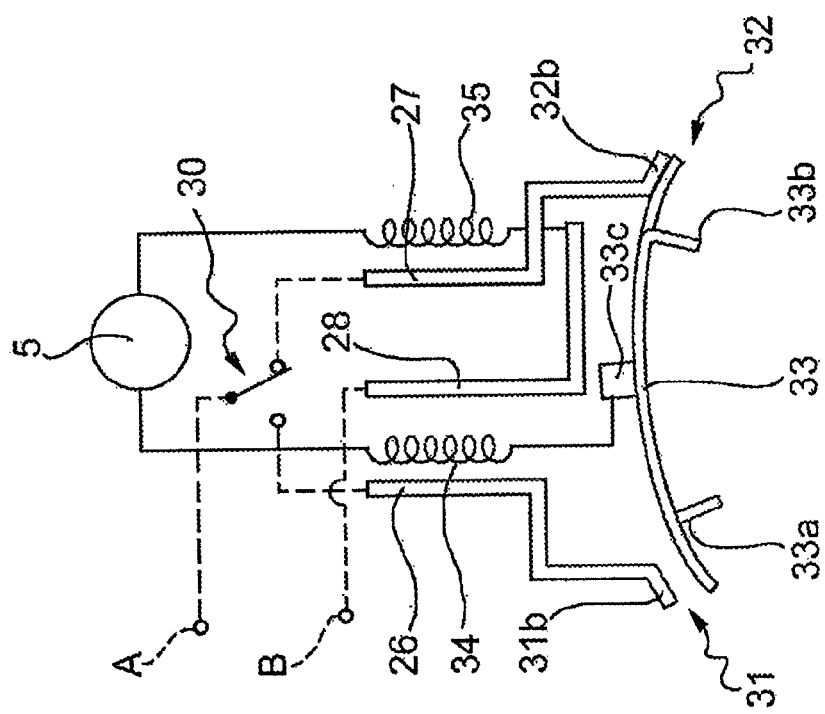

400 # ELECTROMECHANICAL ACTUATOR DEVICE, IN PARTICULAR FOR THE ACTUATION OF FLUID VALVES

BACKGROUND OF THE INVENTION

The present invention relates to an actuator device, in particular for the actuation of fluid valves, for instance boiler or refrigeration plant valves.

An actuator device of this type is known, for instance, from British Patent 2 316 152 in the name of the same Applicant.

The actuator device known from this document comprises two electric switches provided with respective moving contact members controlled by respective feeler members which cooperate with a radial cam profile of a rotary control member. Respective helical recall springs are also associated with each of the feeler members.

This known device is therefore rather complex in structural terms and in terms of its embodiment.

SUMMARY OF THE INVENTION

An object of the present invention is therefore to provide an improved electromechanical actuator device, which has a simpler structure, is easier to assemble and is also more reliable.

These and other objects are achieved according to the invention by an electromechanical actuator device whose salient features are set out in the accompanying claim 1.

BRIEF DESCRIPTION OF THE DRAWINGS

Other advantages and features of the present invention will become clear from the following detailed description, given purely by way of non-limiting example, with reference to the appended drawings, in which:

FIGS. 4a to 4d show part of the actuator device of the preceding drawings, in four different operating conditions;

DETAILED DESCRIPTION OF THE INVENTION

Figure 1:
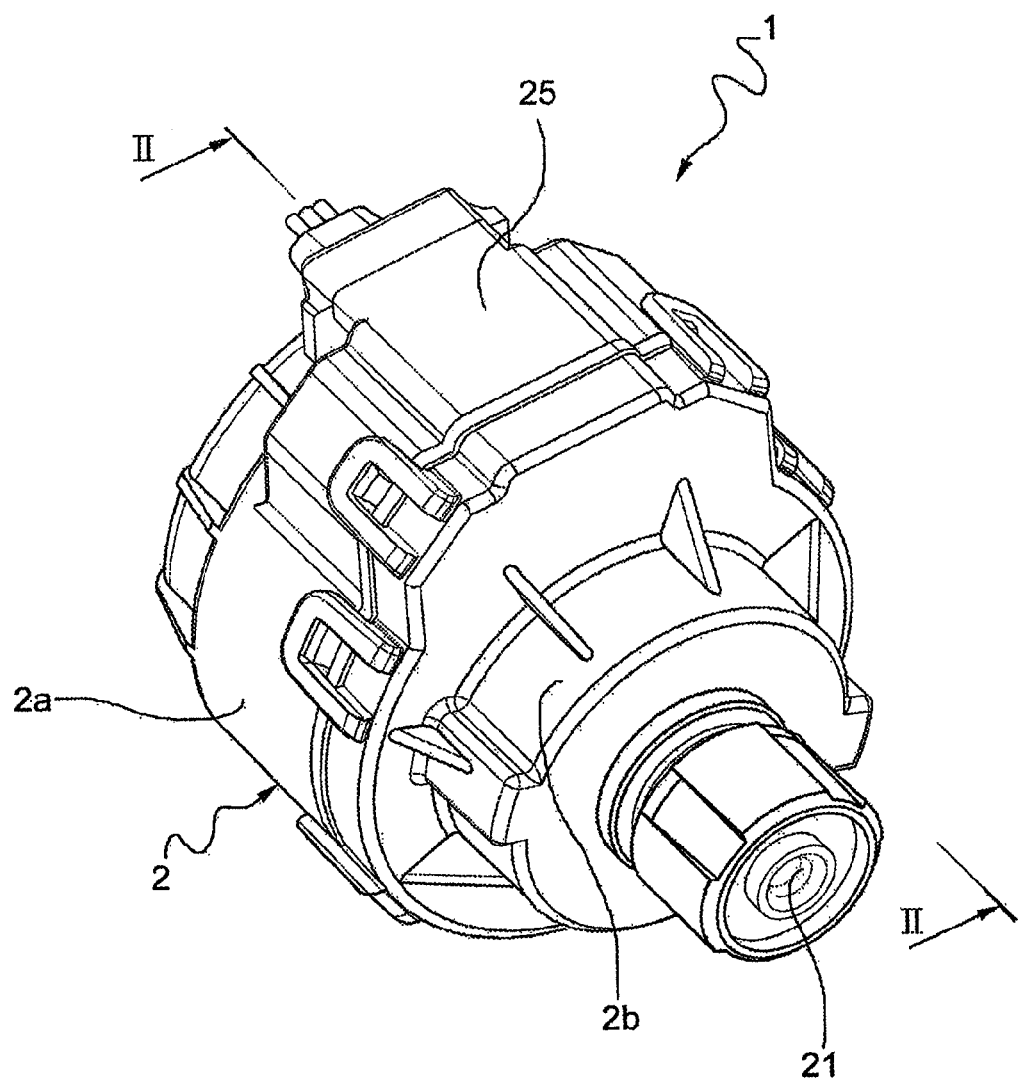
FIG. 1 is a perspective view of an electromechanical actuator device of the invention.
Figure 2:
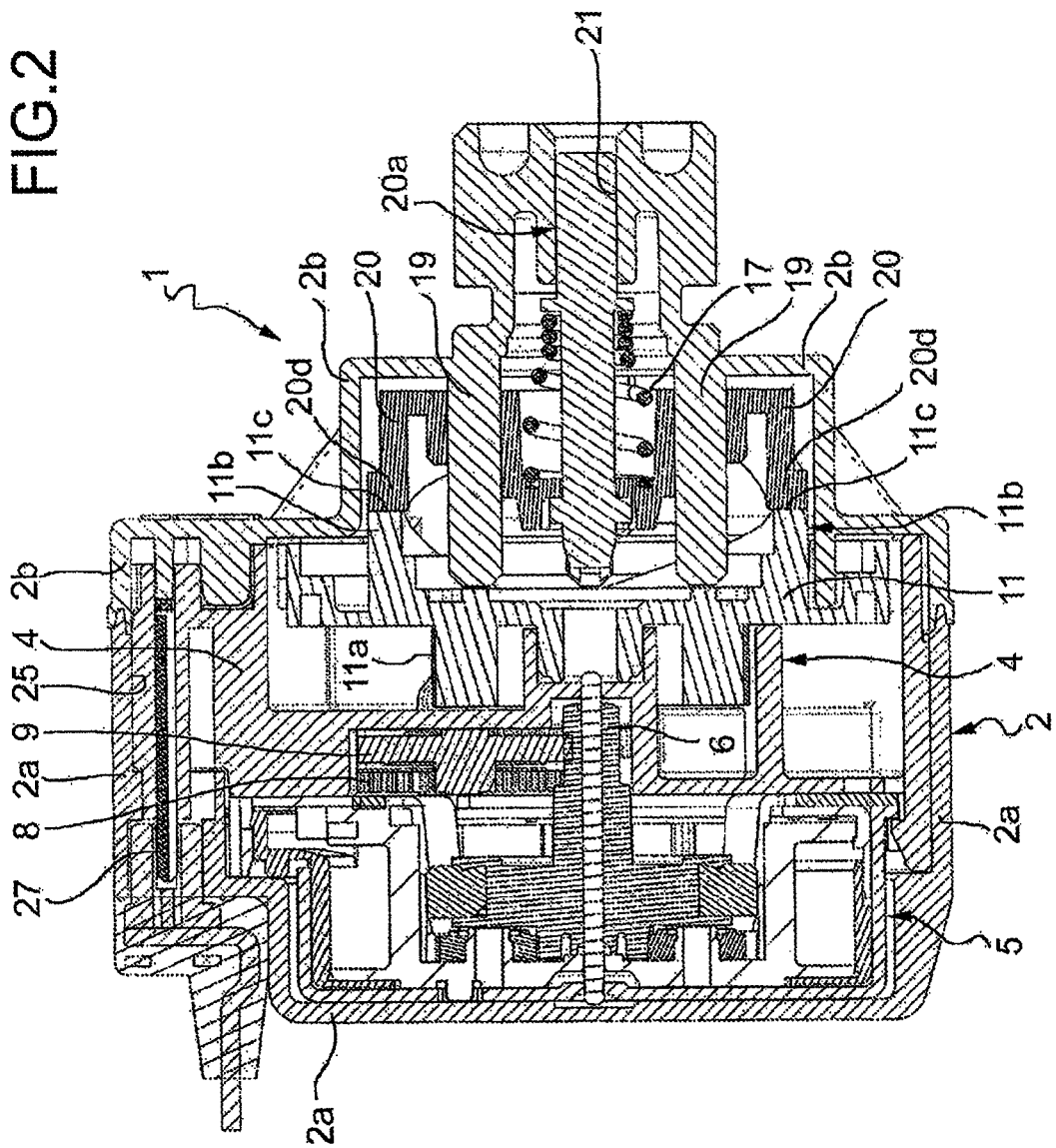
FIG. 2 is a view in cross-section along the line II-II of FIG. 1.
Figure 3:
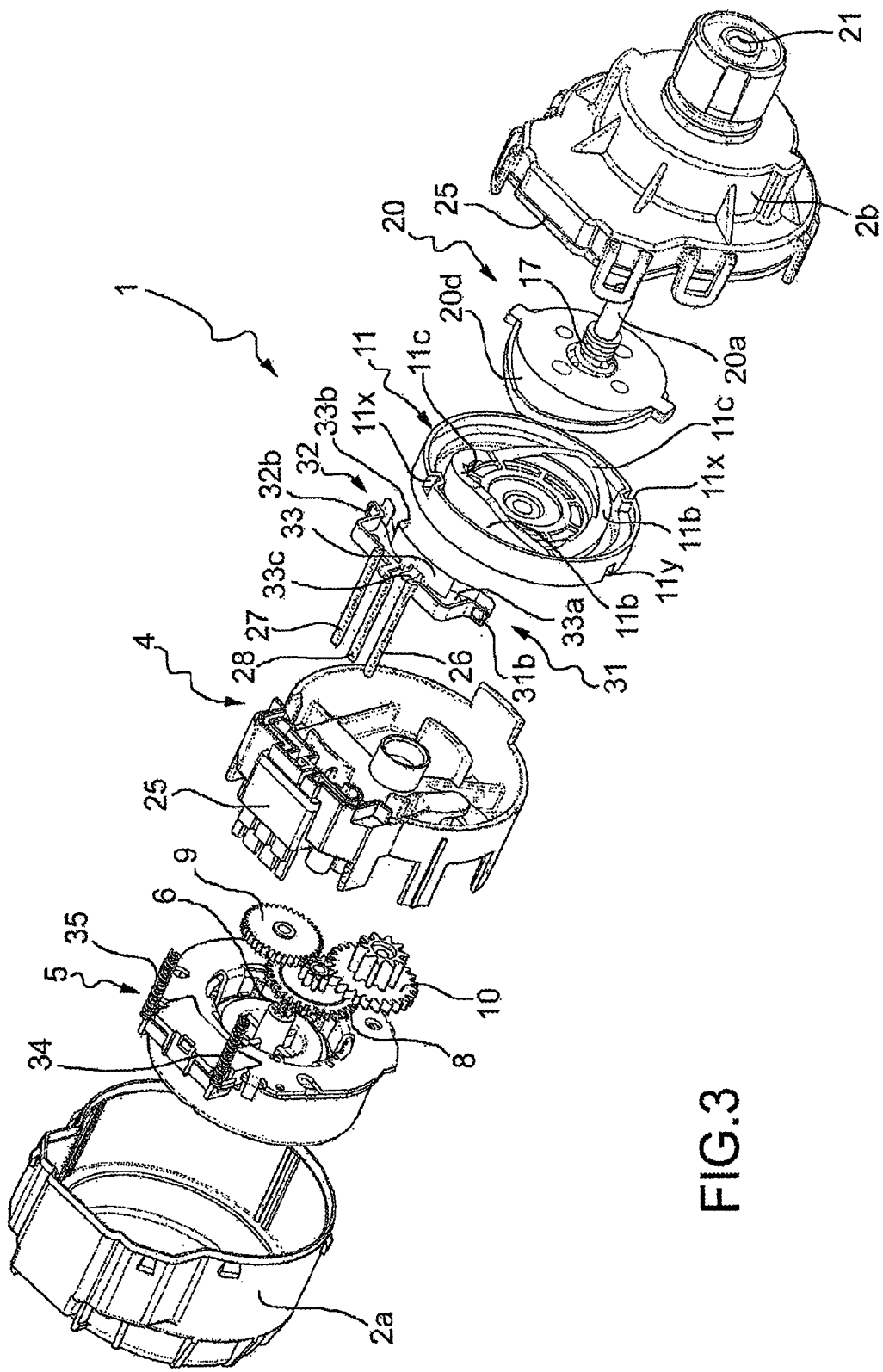
FIG. 3 is a partially exploded perspective view of the actuator device of the preceding drawings.

In the drawings, and in particular FIGS. 1 to 3, an electromechanical actuator device 1 of the invention comprises a support housing 2 advantageously formed by two half-shells 2a and 2b coupled together.

A support structure 4 (FIG. 2) is secured in the housing 2, an electric motor, shown overall by 5, being secured to one surface of this structure. This motor may be of a direct or alternate current type.

The shaft 6 of the electric motor 5 is coupled to a geared transmission which, in the embodiment shown, comprises three toothed wheels 8, 9 and 10 (FIG. 3), each of which has two sets of teeth with different respective diameters.

The set of teeth of smaller diameter of the toothed output wheel 10 engages with a toothed crown 11a (FIG. 2) of a control member (FIGS. 2 and 3) which is mounted to rotate within the housing 2.

On the side opposite to the electric motor 5, the rotary control member 11 has a formation 11b with a cam profile 11c. In the embodiment shown, the front formation 11b comprises two arcuate sectors each having a peripheral extension of approximately 180° and having a respective summit profile which, proceeding from one end to the other, rises progressively from a minimum level to a predetermined maximum level and then drops back to the minimum level at the other end.

With reference to FIG. 2 in particular, within the half-shell 2b, parallel guide pins 19 extend from the latter and a controlled member, shown overall by 20, is mounted on these pins such that it may move in axial translation.

The member 20 bears a central axial pin 20a mounted in a corresponding axial through hole 21 of the half-shell 2b (FIGS. 2 and 3).

The axial pin or rod 20a is adapted to cooperate with a corresponding control pin or rod of a fluid valve to which the actuator device 1 is adapted to be coupled.

On the side facing the rotary control member 11, the controlled member 20 also has a projecting front formation, substantially complementary with the formation 11b of the control member described above. In FIGS. 2 and 3, the two arcuate sectors of the projecting front formation of the controlled member 20 are shown by 20d.

The facing front portions of the control member 11 and the controlled member 20 are such that when the electric motor 5 is actuated, the rotation of the control member 11 is able to cause the controlled member 20 to move in translation. In particular, the controlled member 20 may assume a first position, shown in FIG. 2, remote from the control member 11. When the rotation of the electric motor 5 starts from this first position of the controlled member, further rotation of the electric motor 5 enables the member 20 to move in translation to the second position (not shown in the drawings), close to the close member 11, in which the formations of the members 11 and 20 have penetrated one another. A spring 17, interposed between the half-shell 2b and the member 20 (FIGS. 2 and 3), causes the controlled member 20 to move in translation towards the member 11.

By actuating the electric motor 5, preferably (but not necessarily) in the same direction of rotation, it is therefore possible to cause the controlled member 20 to move from the first to the second position described above, and then from the second to the first position, and so on, in order to control the fluid valve or other device associated with the actuator device 1 by means of the corresponding displacement of the control pin or rod 20a.

With reference to FIGS. 1 to 4, a seat 25 is provided in the support housing 2, between the two half-shells 2a and 2b, into which three electrical terminals 26, 27 and 28 extend (see in particular FIG. 3 and the diagrams of FIGS. 4a-4d). These terminals, as will be explained in more detail below, enable the electric motor 5 to be connected in use to a voltage source (terminals A and B of FIGS. 4a-4d) by means of an external switching control device (shown by 30 in FIGS. 4a-4d) and formed, for instance, by a switch driven by a pressostat.

The switching control device 30 is in particular adapted to assume a first and a second state (FIGS. 4a and 4c respectively) in order to cause the controlled member 20 to pass from the first to the second position described above and, respectively, from the second to the first position.

Two electrical switches, shown overall by 31 and 32 in FIGS. 4a-4d, are also provided in the housing 2 of the actuator device 1.

These switches comprise respective fixed contact members 31b and 32b connected to the connection terminals 26 and 27 respectively.

The switches 31 and 32 comprise a single common moving contact member 33 formed from a single piece of electrically conducting material, in particular a metal material, produced by stamping and bending (see FIG. 3 and, in particular, FIGS. 4a to 4d).

The common moving contact 33 has a substantially bowed shape, with two folded flanges 33a and 33b offset transversely from one another in order to explore, in operation, respective control profiles formed by two adjacent circumferential portions of the periphery of the rotary control member 11 (see FIG. 3 in particular). In the embodiment shown, these circumferential portions have respective pairs of diametrically opposed inlets or recesses 11x, 11y, the recesses 11x of one circumferential portion being angularly offset with respect to the recesses 11y of the other circumferential portion.

As a result of the interaction between the feeler projections 33a and 33b and the associated profiles of the rotary control member 11, the common moving contact 33, in operation, oscillates substantially between two different operating positions, one shown in FIGS. 4a and 4d and the other in FIGS. 4b and 4c. In the first of these positions, the common contact member 33 touches the fixed contact 31b and is remote from the fixed contact 32b.

In the second position described above, the common moving contact 33 is remote from the fixed contact 31b and touches the contact 32b.

In its intermediate portion, the common moving contact 33 has a further flange or projection 33c, folded upwards. This flange or projection 33c is permanently connected to a supply terminal of the electric motor 5 by means of a conducting connection member 34 (FIG. 3) shaped as a helical spring, which extends through the intermediate support structure 4.

The other supply terminal of the electric motor 5 is permanently connected to the connection terminal 28 by means of a similar connection member 35 shaped as a helical spring (see FIG. 3 and the diagrams of FIGS. 4a-4d).

With reference to FIGS. 4a and 4c in particular, the connection terminals 26 and 27 of the actuator device are adapted to be selectively connected to a first terminal A of the voltage source when the external control switch 30 is in the first and respectively the second state shown in these drawings. The connection terminal 28 of the actuator device is, however, adapted to be stably connected to the other terminal B of the voltage source.

The peripheral cam profiles of the rotary control member 11 with which the feeler projections 33a and 33b of the common moving contact 33 cooperate are embodied such that when the external control device 30 is in the first state shown in FIG. 4a, the electric motor 5 may be actuated only if the controlled member 20 is in the first position described above. This state of the actuator device is shown in FIG. 4a: in this state, the electric motor 5 is supplied via the external control switch 30, the connection terminal 26, the switch 31 (which is closed as a result of the position that the control member 11 has imposed on the common moving contact 33), the common moving contact 33, the connection members 34 and 35, and the connection terminal 28. As a result, in this state, the motor 30 causes, via the geared transmission 8-10, the rotation of the control member 11 and the consequent movement in translation of the controlled member 20 until the control member 11 causes, by means of its peripheral profiles, the switching of the common moving contact 33 to the position shown in FIG. 4b. In this state, the supply of current to the electric motor 5 is discontinued and the controlled member 20 remains in the (second) position which it has reached.

If, in this state, the external control member 30 changes state again, i.e. moving to the state shown in FIG. 4c, the electric motor 5 is again actuated, under the action of the current flowing through the external control device 30, the connection terminal 27, the switch 32 (closed), the common moving contact 33, the connection members 34 and 35 and the connection terminal 28. The electric motor 5 then causes a further rotation of the rotary control member 11 and, following cooperation between the respective front formations 11b and 20d of the members 11 and 20, the controlled member 20 moves from the second position described above to the first position again.

On reaching this latter position (FIG. 4d), the peripheral profiles of the control member 11 cause the oscillation of the common moving contact 33 which disengages the fixed contact 32b and re-engages the fixed contact 31b. The supply of current to the motor is thus discontinued and the actuator device stabilises in the state which it has now reached.

The state of the actuator device 1 may change again when the state of the external control device 30 subsequently changes again, moving to the position shown in FIG. 4a.

The operation of the actuator device therefore takes place cyclically, passing through the various states described above with reference to FIGS. 4a to 4d.

Figure 5:
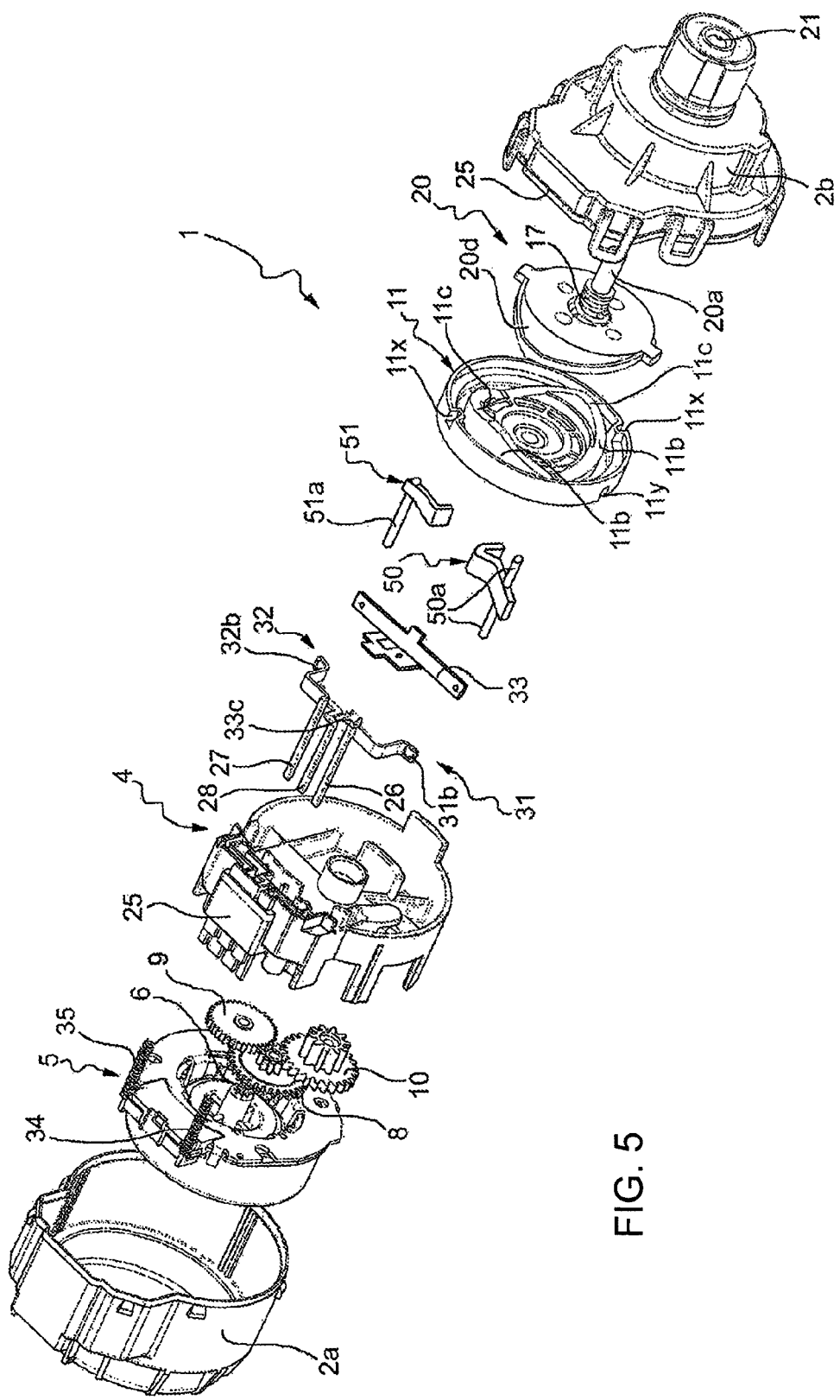
FIG. 5 is a partially exploded perspective view of a variant of the device of the invention.
Figure 6A:
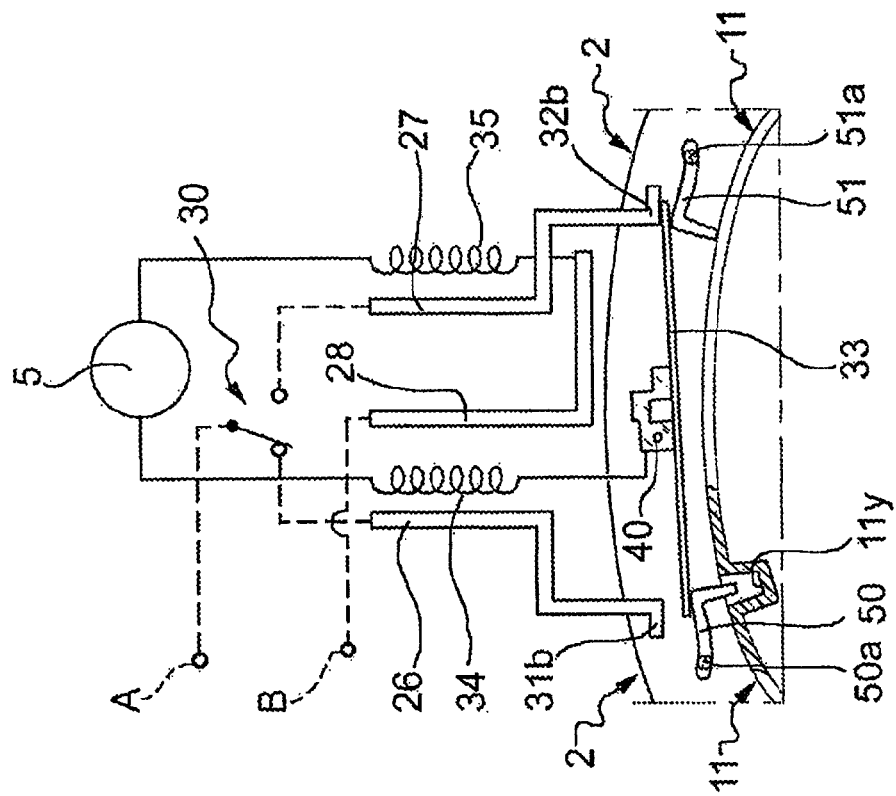
FIGS. 6a and 6b are similar to FIGS. 4a and 4b, but relate to the variant of FIG. 5.
Figure 6B:
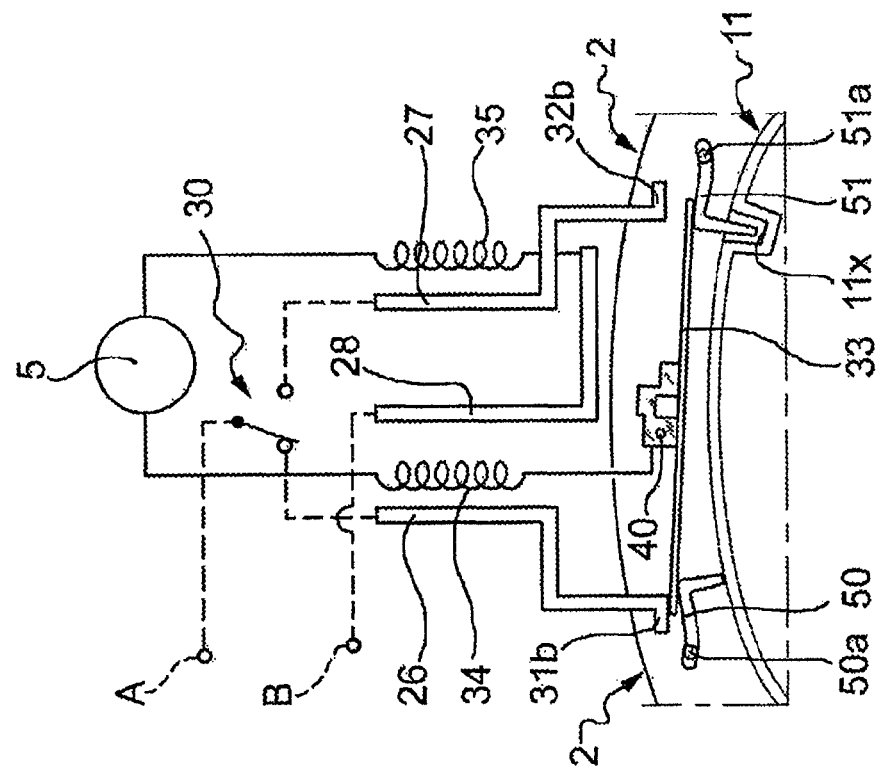

FIGS. 5 and 6a, 6b show a variant. In these drawings, parts and components already described bear the same reference numerals as above.

In this variant, the common moving contact 33 is mounted to oscillate in the support structure or housing about an axis shown by 40 in FIGS. 6a and 6b. In operation, this common contact 33 assumes a position which is controlled by the peripheral circumferential profiles of the member 11 also provided in this case with radial recesses 11x, 11y offset angularly with respect to one another. Control of the position of the common contact 33 and its cooperation selectively with the fixed contact 31b or the fixed contact 32b takes place by means of two feeler members 50, 51 which may oscillate in the housing 2 about the axes of their parallel pins 50a, 51a.

The feelers 50, 51 may be made for instance from a plastics material.

The methods of operation of the variant of FIGS. 5 and 6a, 6b are similar to those of the device illustrated previously and are not therefore described in further detail.

Figure 7:
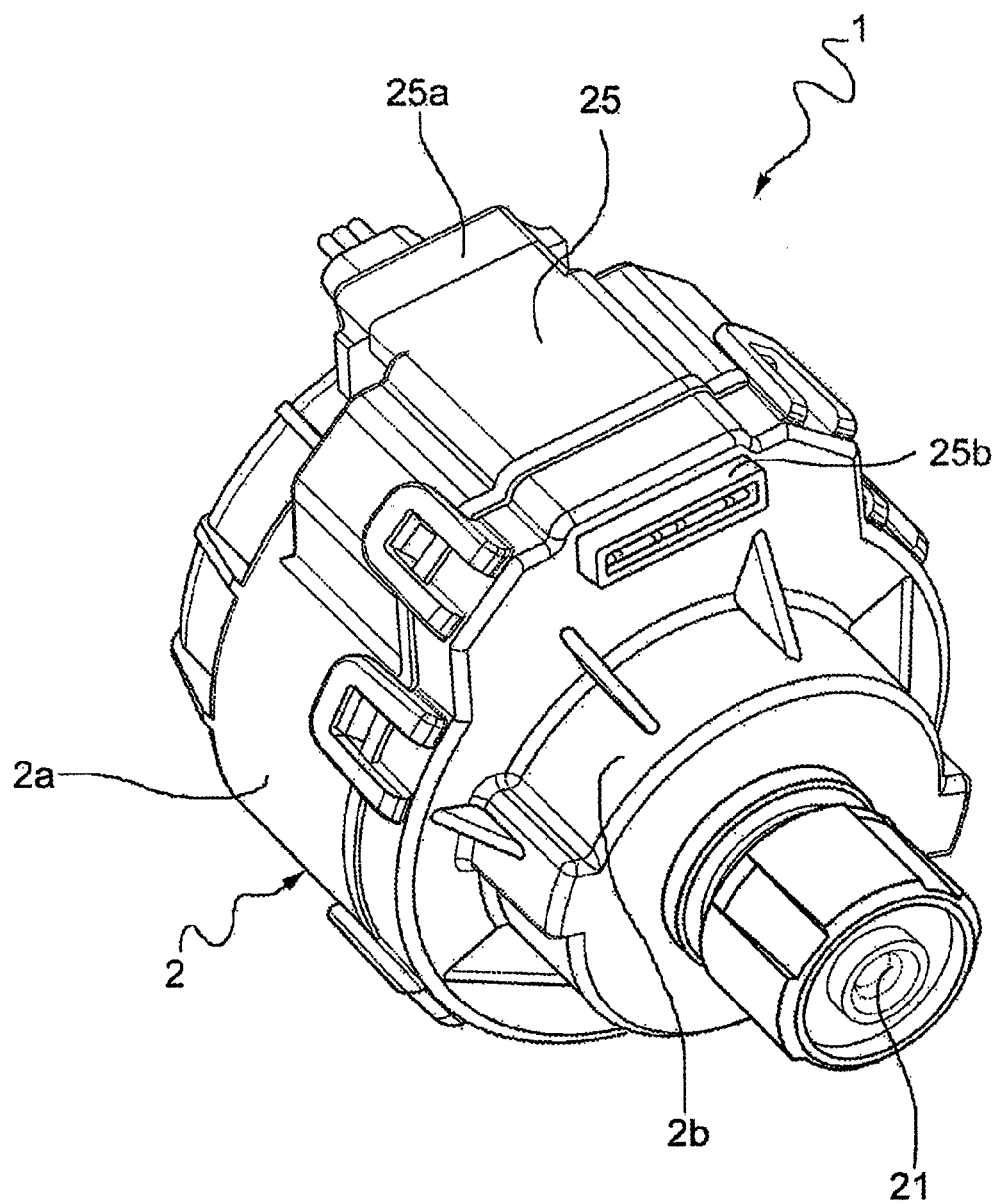
FIG. 7 is a perspective view of a further variant of the device of the invention.

FIG. 7 shows a general variant.

In this variant, the actuator device 1 has been provided with two electrical connectors 25a and 25b provided respectively in the half-shell 2a and the half-shell 2b and facing each other from opposite sides to enable the connection method which is most convenient for the user.

Naturally, the principle of the invention remaining the same, the forms of embodiment and details of construction may be varied widely with respect to those described and illustrated, which have been given purely by way of example, the invention extending to all embodiments which achieve equivalent utility using the same innovative concepts.

The invention claimed is:

1. An actuator device, in particular for the actuation of fluid valves, comprising
    a support housing in which an electric motor is secured, a shaft of this motor being coupled to a rotary control member, one surface of which is provided with a cam profile (11c) cooperating frontally with a coordinated profile of an associated controlled member mounted such that it may move in axial translation in the housing such that when the motor is actuated, the rotation of the rotary control member is adapted to cause the controlled member to move in translation into a first position remote from the control member or to enable this controlled member to move in translation into a second position close to the control member, the housing further bearing electrical connection terminals adapted to enable the connection of the motor to a voltage source by means of an external control device adapted to assume a first and a second state respectively, in order to cause the controlled member to pass from the first to the second position and from the second to the first position respectively, the housing further bearing a first and a second electrical switch connected to the electrical terminals and to the motor and comprising respective fixed contacts and associated moving contact means controlled by associated feeler means which cooperate with corresponding cam profiles of the above-mentioned rotary control member such that when the external control device is in one of the first and second state, the electric motor is actuated if the controlled member is in one of the first and second position and the motor is de-activated when the controlled member reaches the the other of the first and second position, wherein said moving contact means comprise a single moving contact member, common to the first and second switches and made from an electrically conducting material, with which two integral feeler members are associated and cooperate directly with associated cam profiles of the rotary control member.

2. An actuator device according to claim 1, wherein the integral feeler members are folded flanges integral with the common moving contact member.

3. An actuator device according to claim 2, wherein the folded flanges of the common moving contact member are transversely offset with respect to one another.

4. An actuator device according to claim 1, wherein the integral feeler members are separate and remote from the common moving contact member and are mounted to oscillate about respective axes in the support housing.

5. An actuator device according to claim 1, comprising electrical connector means for connection to a voltage source and to external control devices, the actuator device being characterized in that the connector means comprise a first and a second electrical connector provided in the support housing and facing each other on opposite sides.

* * * * *